United States Patent [19]

Nagano et al.

[11] Patent Number: 4,579,688

[45] Date of Patent: Apr. 1, 1986

[54] N-(2-FLUORO-4-HALO-5-SUBSTITUTED PHENYL)HYDANTOINS, AND THEIR PRODUCTION AND USE

[75] Inventors: Eiki Nagano, Nishinomiya; Shunichi Hashimoto, Toyonaka; Ryo Yoshida, Kawanishi; Hiroshi Matsumoto, Toyonaka; Katsuzo Kamoshita, Osaka, all of Japan

[73] Assignee: Sumitomo Chemical Company, Limited, Osaka, Japan

[21] Appl. No.: 549,439

[22] Filed: Nov. 7, 1983

Related U.S. Application Data

[62] Division of Ser. No. 383,293, May 28, 1982, Pat. No. 4,427,438.

[30] Foreign Application Priority Data

May 29, 1981 [JP] Japan ................... 56-83313

[51] Int. Cl.$^4$ ............... C07C 122/00; A01N 43/48
[52] U.S. Cl. ........................... 560/358; 71/92
[58] Field of Search ................... 260/453 AR

[56] References Cited

U.S. PATENT DOCUMENTS 3,704,307  11/1972  Zecher et al. ............... 260/453 AR
3,749,746   7/1973  Duerr ........................... 260/453 AR
3,758,481   9/1973  Hya et al. .................... 260/453 AR
4,427,438   1/1984  Nagano et al. .............. 260/453 AR

FOREIGN PATENT DOCUMENTS 0008052  1/1983  Japan ........................... 260/453 AR Primary Examiner—Alan Siegel
Attorney, Agent, or Firm—Birch, Stewart, Kolasch & Birch

[57] ABSTRACT

A composition comprising an N-(2-fluoro-4-halo-5-substituted phenyl)hydantoin of the formula:

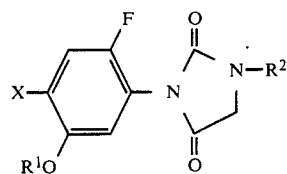

wherein X is a chlorine atom or a bromine atom and $R^1$ and $R^2$ are, same or different, each a $C_1$–$C_4$ alkyl group, a cyclopropyl group, a $C_3$–$C_4$ alkenyl group or a $C_3$–$C_4$ alkynyl group and an inert carrier, which is useful as a herbicide.

9 Claims, No Drawings

N-(2-FLUORO-4-HALO-5-SUBSTITUTED PHENYL)HYDANTOINS, AND THEIR PRODUCTION AND USE

This application is a divisional of copending application Ser. No. 383,293, filed on May 28, 1982 U.S. Pat. No. 4,427,438.

The present invention relates to N-(2-fluoro-4-halo-5-substituted phenyl)hydantoin (hereinafter referred to as "hydantoin(s)"), and their production and use.

The said hydantoins are representable by the formula:

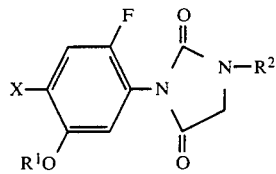
(I)

wherein X is a chlorine atom or a bromine atom and $R^1$ and $R^2$ are the same or different, and each is a $C_1$–$C_4$ alkyl group, a cyclopropyl group, a $C_3$–$C_4$ alkenyl group or a $C_3$–$C_4$ alkynyl group.

It is known that certain kinds of N-phenylhydantoins are effective as herbicides. For instance, the herbicidal use of 3-(4-chlorophenyl)-1-methylhydantoin, 3-(4-chlorophenyl)-1-allylhydantoin, 3-(2,4-dichlorophenyl)-1-allylhydantoin, etc. is disclosed in U.S. Pat. No. 3,134,663, Japanese Patent Publication (examined) No. 30695/1975, etc. However, their herbicidal effect is still not always satisfactory.

It has now been found that the hydantoins (I) show a strong herbicidal activity against a wide variety of weeds including Gramineae weeds, Cyperaceae weeds and broad-leaved weeds at small doses and do not produce any material phytotoxicity on various agricultural crops. Examples of Gramineae weeds against which the hydantoines (I) show a herbicidal activity are barnyardgrass (*Echinochloa crus-galli*), green foxtail (*Setaria viridis*), large crabgrass (*Digitaria sanguinalis*), Johnsongrass (*Sorghum halepense*), wild oat (*Avena fatua*), water foxtail (*Alopecurus geniculatus*), goosegrass (*Eleusine indica*), annual bluegrass (*Poa annua*), bermudagrass (*Cynodon dactylon*), quackgrass (*Agropyron repens*), etc. Examples of Cyperaceae weeds are nutsedge sp. (Cyperus sp.), *Cyperus rotundus, Ceperus esculentus,* hardstem bulrush (*Scirpus juncoides*), nutsedge (*Cyperus serotinus*), water chestnut (*Eleocharis kuroguwai*), slender spikerush (*Eleocharis acicularis*), etc. Examples of broad-leaved weeds are tall morningglory (*Ipomoea purpurea*), velvetleaf (*Abutilon theophrasti*), sicklepod (*Cassia obtusifolia*), wild sunflower (*Helianthus annus*), cocklebur (*Xanthium pennsylvanicum*), wild mustard (*Brassica kaber*), common chickweed (*Stellaria media*), common purslane (*Portulaca oleracea*), jimsonweed (*Datura stramonium*), hemp sesbania (*Sesbania exaltata*), sun spurge (*Euphorbia helioscopia*), black nightshade (*Solanum nigrum*), prickly sida (*Sida spinosa*), common ragweed (*Ambrosia artemisifolia*), smartweed sp. (Polygonum sp.), redroot pigweed (*Amaranthus retroflexus*), bedstraw (*Galium aparine*), pineappleweed (Matricaria spp.), birdseye speedwell (*Veronica persica*), wild buckwheat (*Polygonum convolvulus*), beggarticks (Bidens spp.) common lambsquarters (*Chenopodium album*), bindweed (*Calystegia japonica*), monochoria (*Monochoria vaginalis*), *Dopatrium junceum,* waterwort (*Elatine triandra*), false pimpernel (*Lindernia procumbens*), toothcup (*Rotala indica*), arrowhead (*Sagittaria pygmaea*), etc. Accordingly, the hydantoines (I) can be used as herbicides applicable to paddy fields as well as agricultural plowed fields. They are also useful as herbicides to be employed for orchard, tea garden, mulberry field, rubber plantation, forest, lawn, pasture, non-agricultural field, etc and other applications.

The hydantoins (I) can be produced by reacting a phenyl isocyanate of the formula:

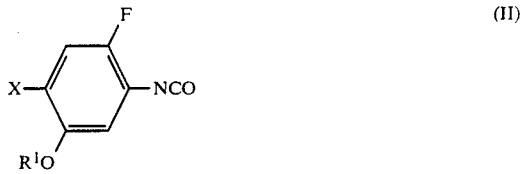
(II)

wherein X and $R^1$ are each as defined above with an aminoacetonitrile of the formula:

(III)

wherein $R^2$ is as defined above in the presence of an inert solvent (e.g. benzene, toluene, xylene, ligroin, hexane) at a temperature from room temperature (ca. 20° C.) to the boiling temperature of the solvent to give a phenylurea of the formula:

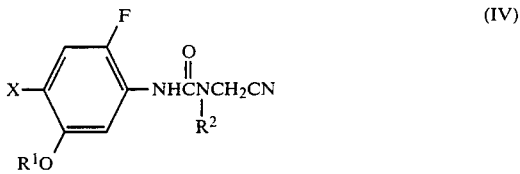
(IV)

wherein X, $R^1$ and $R^2$ are each as defined above, followed by treatment of the latter with a catalytic amount of a mineral acid, preferably hydrochloric acid, at a temperature from room temperature (ca. 20° C.) to about 100° C. for cyclization.

The thus produced hydantoins (I) may be, when desired, purified by a per se conventional procedure such as recrystallization or column chromatography.

The phenyl isocyanate (II) as one of the starting materials can be produced by reacting an aniline of the formula:

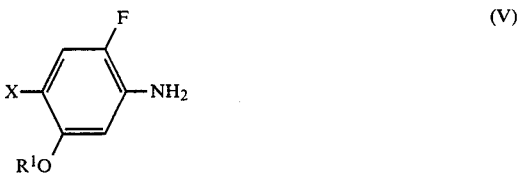
(V)

wherein X and $R^1$ are each as defined above with an equimolar or excessive amount of phosgene in an inert solvent (e.g. benzene, toluene, xylene, ligroin, hexane, ethyl acetate, carbon tetrachloride, dioxane, tetrahydrofuran) at a temperature from room temperature (ca. 20° C.) to the boiling temperature of the solvent.

The aminoacetonitrile (III) as the starting material may be produced easily by a conventional method as disclosed in Japanese Patent Publn. (unexamined) Nos. 122750/1980 and 122751/1980. Namely, the reaction between glyconitrile and a primary amine gives the aminoacetonitrile (III).

Production of the aniline (V) can be carried out from a phenol of the formula:

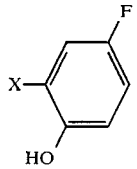

(VI)

wherein X is as defined above [J.Am.Chem.Soc., 81, 94 (1959)] according to the following scheme:

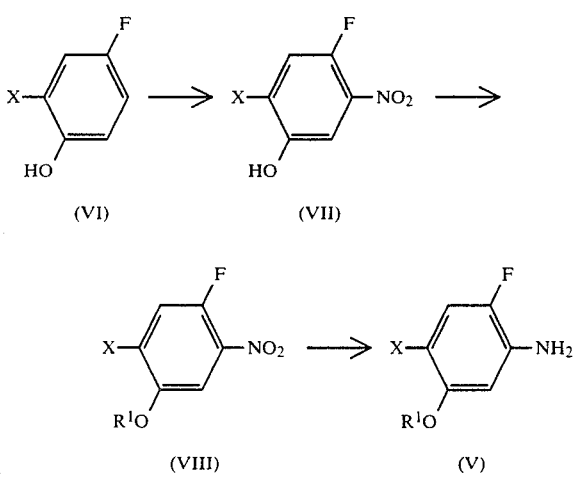

wherein X and $R^1$ are each as defined above.

In the above scheme, the conversion of the phenol (VI) into the nitrophenol (VII) is attained by nitration. The nitration may be accomplished, for instance, by reacting the phenol (VI) in the form of an alkali metal salt (e.g. sodium salt, potassium salt) with alkyl haloformate (e.g. methyl chloroformate, ethyl chloroformate) in an aqueous medium at a temperature of 0° to 10° C. to give a phenol carbonate of the formula:

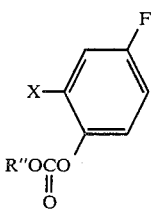

wherein R″ is lower alkyl (e.g. methyl, ethyl) and X is as defined above and reacting the phenol carbonate with concentrated nitric acid in the presence of concentrated sulfuric acid at room temperature (ca. 20° C.) to give a nitrophenol carbonate of the formula:

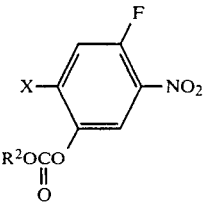

wherein X and $R^2$ are each as defined above, followed by treating the nitrophenol carbonate with an aqueous alkali such as aqueous sodium hydroxide at a temperature of 40° to 80° C. for hydrolysis.

The conversion of the nitrophenol (VII) into the nitrobenzene (VIII) is achieved by reacting the former in the form of an alkali metal salt with a halide of the formula: $R^1Y$ wherein Y is halogen and $R^1$ is as defined above in an inert solvent (e.g. water, dimethylformamide, acetonitrile, acetone, dimethylsulfoxide) at a temperature of 10° to 200° C., preferably of 30° to 100° C. The presence of a phase transfer catalyst (e.g. tetrabutylammonium bromide) in the reaction system is favorable to effect the reaction smoothly. Formation of the alkali metal salt of the nitrophenol (VII) may be carried out by a conventional procedure, i.e. treatment of the nitrophenol (VII) in a free form with alkali metal carbonate (e.g. potassium carbonate), alkali metal hydroxide (e.g. sodium hydroxide), alkali metal hydride (e.g. sodium hydride) or alkali metal alkoxide (e.g. sodium methoxide, sodium ethoxide) in an inert solvent.

The conversion of the nitrobenzene (VIII) into the aniline (V) may be performed by various reduction procedures. When the substituent $R^1$ is $C_1$-$C_4$ alkyl, there may be adopted any conventional reduction procedure for converting a nitro group on the benzene ring into an amino group such as reduction with sodium sulfide, reduction with iron powder or catalytic reduction. One of the typical procedures comprises introduction of a 3 molar amount of hydrogen into a reaction system comprising one molar amount of the nitrobenzene (VIII) and a 1/10 to 1/100 molar amount of platinum dioxide at room temperature (ca. 20° C.) under atmospheric pressure. Another typical procedure comprises admixing an acetic acid solution containing one molar amount of the nitrobenzene (VIII) with a 5% acetic acid solution containing a 2.5 to 5 molar amount of iron powder such as reductive iron or electrolytic iron and effecting the reaction at a temperature of 80° to 100° C.

When the substituent $R^1$ is $C_3$-$C_4$ alkenyl or $C_3$-$C_4$ alkynyl, the adopted method may be reduction with iron powder. For instance, an acetic acid solution containing one molar amount of the nitrobenzene (VIII) is admixed with a 5% acetic acid solution containing 2.5 to 5 molar amount of iron powder such as reductive iron or electrolytic iron at a temperature of 80° to 100° C., followed by agitation at a temperature of 80° to 120° C., preferably of 90° to 110° C., for a period of 0.5 to 5 hours.

Practical and presently preferred embodiments of the production of the objective hydantoins (I) as well as the intermediary compounds are illustratively shown below:

EXAMPLE 1

Production of the hydantoin (I: X=Cl; R¹=iso-C₃H₇—; R²=iso-C₃H₇—):

A solution of 4-chloro-2-fluoro-5-isopropoxyphenyl isocyanate (3.54 g) in toluene (20 ml) was dropwise added to a solution of N-isopropylaminoacetonitrile (2.56 g) in toluene (30 ml) at 50° to 60° C., and the resultant mixture was refluxed for 3 hours under heating. The reaction mixture was allowed to cool to room temperature (ca. 20° C.) and conc. hydrochloric acid (10 ml) was added thereto, followed by reflux for 3 hours. After being allowed to stand at room temperature, the toluene layer was separated, and the aqueous layer was extracted with toluene. The extract was combined with the toluene layer, washed with water, dried over anhydrous magnesium sulfate and concentrated. The residue was purified by chromatography with silica gel to give 1.2 g of 3-(4-chloro-2-fluoro-5-isopropoxyphenyl)-1-isopropylimidazolidine-2,4-dione (Compound No. 5) as colorless crystals. M.P., 70.5°–71.4° C.

NMR (CDCl₃) δ (ppm): 1.25 (6H, d, J=6 Hz), 1.35 (6H, d, J=6 Hz), 3.9 (2H, s), 4.1–4.6 (2H, m), 6.85 (1H, d, J=6 Hz), 7.25 (1H, d, J=10 Hz).

Examples of the hydantoin (I) produced in the same manner as above are shown in Table 1.

gene/toluene solution (500 ml) at room temperature (ca. 20° C.), followed by heating under reflux for 2 hours. The mixture was concentrated under reduced pressure and the residue was distilled to give 26 g of 4-chloro-2-fluoro-5-isopropoxyphenyl isocyanate as pale yellow crystals. M.P., 36°–37° C. B.P., 90°–91° C./3 mmHg.

IR $\nu_{max}$ (cm⁻¹): 2240.

Some examples of the phenyl isocyanate (II) produced in the same manner as above are shown in Table 2.

TABLE 2

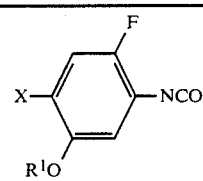

| X | R¹ | Physical property |
|---|---|---|
| Cl | CH₃— | M.P. 42°–44.5° C. |
| Cl | n-C₃H₇— | M.P. 43°–44° C. |
| Cl | iso-C₃H₇— | M.P. 36°–37° C. |
| Br | C₂H₅— | M.P. 35°–36.5° C. |
| Cl | CH₂=CHCH₂— | B.P. 107° C./3 mmHg; $n_D^{16}$ 1.5481 |
| Cl | CH≡CCH₂— | M.P. 61.5°–62.5° C. |
| Cl | sec-C₄H₉— | B.P. 102° C./1 mmHg; $n_D^{22.0}$ 1.5200 |

TABLE 1

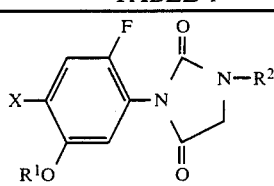

(I)

| Compound No. | R¹ | R² | X | Physical property |
|---|---|---|---|---|
| 1 | CH₃— | iso-C₃H₇— | Cl | M.P. 117.2°–118.2° C. |
| 2 | n-C₃H₇— | iso-C₃H₇— | Cl | M.P. 136°–137° C. |
| 3 | iso-C₃H₇— | CH₃— | Cl | M.P. 107°–108° C. |
| 4 | iso-C₃H₇— | C₂H₅— | Cl | M.P. 88.6°–90.5° C. |
| 5 | iso-C₃H₇— | iso-C₃H₇— | Cl | M.P. 70.5°–71.4° C. |
| 6 | iso-C₃H₇— | cyclo-C₃H₅— | Cl | M.P. 81.3°–83.0° C. |
| 7 | iso-C₃H₇— | CH₂=CHCH₂— | Cl | $n_D^{21.0}$ 1.5351<br>NMR δ (ppm): 1.35 (6H, d, J = 6Hz), 3.95 (2H, s) 4.05 (2H, d, J = 6Hz), 4.4 (1H, m, J = 6Hz), 6.80 (1H, d, J = 6Hz), 7.2 (1H, d, J = 10Hz) |
| 8 | iso-C₃H₇— | t-C₄H₉— | Cl | Wax-like substance<br>NMR δ (ppm): 1.32 (6H, d, J = 6Hz), 1.48 (9H, s), 4.05 (2H, s), 4.45 (1H, m, J = 6Hz), 6.85 (1H, d, J = 6Hz), 7.22 (1H, d, J = 10Hz) |
| 9 | C₂H₅— | iso-C₃H₇— | Cl | M.P. 103°–104.3° C. |
| 10 | iso-C₃H₇— | CH≡CCH₂— | Cl | M.P. 106°–107° C. |
| 11 | iso-C₃H₇— | n-C₃H₇— | Cl | $n_D^{27}$ 1.5251<br>NMR δ (ppm): 0.9 (3H, t, J = 6Hz), 1.3 (6H, d, 6Hz), 1.4–1.7 (2H, m), 3.35 (2H, t, J = 7Hz), 4.0 (2H, s), 4.4 (1H, m), 6.85 (1H, d, J = 6Hz), 7.2 (1H, d) |
| 12 | CH₂=CHCH₂— | sec-C₄H₉— | Cl | $n_D^{23.5}$ 1.5378 |
| 13 | CH≡CCH₂— | iso-C₃H₇— | Cl | M.P. 139°–143° C. |
| 14 | sec-C₄H₉— | CH₃— | Cl | M.P. 90.5°–97.5° C. |
| 15 | C₂H₅— | CH₃— | Br | M.P. 94.0°–97.5° C. |
| 16 | iso-C₃H₇— | CH₃— | Br | M.P. 93°–94° C. |
| 17 | CH≡CCH₂— | iso-C₃H₇— | Br | M.P. 117.0°–122° C. |

EXAMPLE 2

Production of the phenyl isocyanate (II: X=Cl; R¹=iso-C₃H₇—):

A solution of 4-chloro-2-fluoro-5-isopropoxyaniline (30 g) in toluene (100 ml) was added to a 1 mol/l phos-

EXAMPLE 3

Production of the aniline (V: X=Cl; R¹=iso-C₃H₇—):

A suspension of 4-chloro-2-fluoro-5-isopropoxynitrobenzene (13.5 g) and platinum dioxide (0.4 g) in ethanol (300 ml) was subjected to catalytic reduction with hydrogen at room temperature (ca. 20° C.) under atmospheric pressure, whereby a designated amount of hydrogen was absorbed. The resultant mixture was filtered to remove insoluble materials, and the filtrate was concentrated. The residue was subjected to purification by silica gel chromatography to give 5.6 g of 4-chloro-2-fluoro-5-isopropoxyphenylaniline. $n_D^{24.5}$ 1.5360.

NMR (CDCl$_3$) δ (ppm): 1.3 (6H, d, J=6 Hz), 3.7 (2H, m, J=1.5 Hz), 4.35 (1H, q, J=6 Hz), 6.45 (1H, d, J=7 Hz), 7.1 (1H, d, J=10 Hz).

IR $\nu_{max}$ (cm$^{-1}$): 3450, 3550.

EXAMPLE 4

Production of the aniline (V: X=Cl, R$^1$=CH≡CCH$_2$—):

A suspension of electrolytic iron powder (3.5 g) in a 5% aqueous acetic acid solution was heated to 90° C., and a solution of 4-chloro-2-fluoro-5-(2-propynyloxy)-nitrobenzene (5.7 g) in acetic acid (40 ml) was dropwise added thereto at the same temperature. The resultant mixture was stirred for at 90°–105° C. for 1 hour and allowed to cool to room temperature. Water (200 ml) was added thereto. Insoluble materials were filtered off, and the filtrate was neutralized, followed by extraction with ethyl acetate. The extract was dried over anhydrous magnesium sulfate and concentrated. The residue was washed with petroleum ether and carbon tetrachloride to give 3.6 g of 4-chloro-2-fluoro-5-(2-propynyloxy)aniline. M.P. 61.0°–61.5° C.

NMR (CDCl$_3$) δ (ppm): 2.5 (1H, t, J=2 Hz), 3.4–4.2 (2H, m, J=16 Hz), 4.15 (2H, d, J=2 Hz), 6.5 (1H, d, J=8 Hz), 6.95 (1H, d, J=10 Hz).

IR $\nu_{max}$ (cm$^{-1}$): 3460, 3360, 3280, 2100.

Some examples of the aniline (V) produced in the same manner as above are shown in Table 3.

TABLE 3

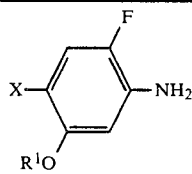

| X | R$^1$ | Physical property |
|---|---|---|
| Cl | C$_2$H$_5$— | $n_D^{24.5}$ 1.5503 |
| Br | C$_2$H$_5$— | $n_D^{24.5}$ 1.5680 |
| Cl | n-C$_3$H$_7$— | $n_D^{24.5}$ 1.5386 |
| Br | n-C$_3$H$_7$— | $n_D^{24.5}$ 1.5618 |
| Cl | iso-C$_3$H$_7$— | $n_D^{24.5}$ 1.5360 |
| Br | iso-C$_3$H$_7$— | $n_D^{24.5}$ 1.5547 |
| Cl | CH$_2$=CHCH$_2$— | $n_D^{24.5}$ 1.5598 |
| Cl | CH≡CCH$_2$— | M.P. 61.0°–61.5° C. |
| Cl | CH≡C—CH— <br> \| <br> CH$_3$ | M.P. 67.0°–68° C. |

EXAMPLE 5

Production of the nitrobenzene (VIII: X=Cl; R$^1$=iso-C$_3$H$_7$—):

To a solution of 2-chloro-4-fluoro-5-nitrophenol (19.1 g) in acetonitrile (100 ml), there was added anhydrous potassium carbonate (8 g). After stirring at room temperature (ca. 20° C.) for several minutes, isopropyl iodide (25 g) was added thereto, and the resultant mixture was heated under reflux for 3 hours. After being allowed to cool to room temperature (ca. 20° C.), water was added thereto, and the reaction mixture was extracted with ether. The ether extract was washed with a 5% aqueous sodium hydroxide solution and water in order, dried over anhydrous magnesium sulfate and filtered. The filtrate was concentrated under reduced pressure, and the residue was recrystallized from ethanol to give 13.5 g of 4-chloro-2-fluoro-5-isopropoxynitrobenzene. M.P., 61.3°–62.4° C.

NMR (CDCl$_3$) δ (ppm): 1.42 (6H, d, J=7 Hz), 4.3–4.8 (1H, m), 7.28 (1H, d, J=10 Hz), 7.48 (1H, d, J=6 Hz).

EXAMPLE 6

Production of the nitrobenzene (VIII: X=Cl; R$^1$=CH$_3$—):

To a mixture of 2-chloro-4-fluoro-5-nitrophenol (9.6 g) and potassium carbonate (3.8 g) in acetonitrile (50 ml), there was added methyl iodide (14 g), and the resultant mixture was heated under reflux for 3 hours. After being allowed to cool to room temperature (ca. 20° C.), water was added thereto, and the resulting mixture was extracted with ether. The ether extract was washed with water, dried and concentrated. The residue was recrystallized from ethanol to give 8.9 g of 4-chloro-2-fluoro-5-methoxynitrobenzene. M.P., 67.5°–69.8° C.

NMR (CDCl$_3$) δ (ppm): 3.8 (3H, s), 7.25 (1H, d, J=10 Hz), 7.48 (1H, d, J=6 Hz).

Some examples of the nitrobenzene (VIII) produced in the same manner as above are shown in Table 4.

TABLE 4

| X | R$^1$ | Physical property |
|---|---|---|
| Cl | —CH$_3$ | M.P. 67.5°–69.8° C. |
| Br | —CH$_3$ | M.P. 72.2° C. |
| Cl | —CH$_2$CH$_3$ | M.P. 47°–48° C. |
| Br | —CH$_2$CH$_3$ | M.P. 46°–46.5° C. |
| Cl | —CH$_2$CH$_2$CH$_3$ | M.P. 46°–47° C. |
| Br | —CH$_2$CH$_2$CH$_3$ | M.P. 46.8°–47.4° C. |
| Cl | —CH(CH$_3$)$_2$— | M.P. 61.3°–62.4° C. |
| Br | —CH(CH$_3$)$_2$ | M.P. 65.5°–66.5° C. |
| Cl | —CH(CH$_3$)CH$_2$CH$_3$ | M.P. 59.6°–60.6° C. |
| Cl | —CH$_2$CH=CH$_2$ | $n_D^{17.0}$ 1.5601 |
| Cl | —CHCH=CH$_2$ <br> \| <br> CH$_3$ | M.P. 41.0°–41.5° C. |
| Cl | —CH$_2$C≡CH | M.P. 88°–89° C. |
| Cl | —CHC≡CH <br> \| <br> CH$_3$ | M.P. 87°–88° C. |

EXAMPLE 7

Production of the nitrophenol (VII: X=Cl):

2-Chloro-4-fluorophenol (83.4 g) was added to a solution of sodium hydroxide (27.7 g) in water (450 ml), and methyl chloroformate (69.2 g) was dropwise added thereto at a temperature of below 10° C. Precipitated crystals were collected by filtration and washed with water to give methyl (2-chloro-4-fluorophenyl)formate (134.8 g). M.P., 69°–71° C.

Methyl (2-chloro-4-fluorophehyl)formate (134.8 g) obtained above was suspended in concentrated sulfuric acid (50 ml). To the suspension, a mixture of concentrated sulfuric acid (50 ml) and concentrated nitric acid (50 ml) was added at about 30° C., and the mixture was stirred for at this temperature for 1 hour. The reaction mixture was poured into ice water, and precipitated crystals were collected and washed with water to give methyl (2-chloro-4-fluoro-5-nitrophenyl)formate (143 g). M.P., 53°–55° C.

The product obtained as above was combined with sodium hydroxide (27 g) and water (300 ml), and the resultant mixture was refluxed for 4 hours. Precipitated insoluble materials were filtered using a celite, and the filtrate was acidified with concentrated hydrochloric acid. Precipitated crystals were collected by filtration and washed with water to obtain 76.3 g of 2-chloro-4-fluoro-5-nitrophenol. M.P. 106°–107° C.

NMR (CDCl$_3$, D$_6$-DMSO) δ (ppm): 7.25 (1H, d, J=10 Hz), 7.64 (1H, d, J=6 Hz).

IR $\nu_{max}^{nujol}$ (cm$^{-1}$): 3370.

EXAMPLE 8

Production of the nitrophenol (VII: X=Br):

2-Bromo-4-fluorophenol (28 g) was added to a solution of sodium hydroxide (7 g) in water (100 ml), and methyl chloroformate was dropwise added thereto at a temperature of below 10° C. Precipitated crystals were collected by filtration and washed with water to give methyl (2-bromo-4-fluorophenyl)formate (41 g). M.P., 80.7° C.

The above obtained product was suspended in conc. sulfuric acid (13 ml), a mixture of conc. sulfuric acid (13 ml) and conc. nitric acid (13 ml) was added thereto at about 30° C. and the resulting mixture was stirred for 30 minutes. The reaction mixture was poured onto ice. Precipitated crystals were thoroughly washed with water, whereby yellow crystals of methyl (2-bromo-4-fluoro-5-nitrophenyl)formate (38.3 g) were obtained. M.P., 63.5°–64.5° C.

A mixture of the product thus obtained and sodium hydroxide (6.2 g) in water (100 ml) was refluxed for 3 hours. Insoluble materials were filtered off, and the filtrate was acidified with hydrochloric acid. Precipitated crystals were collected by filteration and washed with water to obtain 25 g of 2-bromo-4-fluoro-5-nitrophenol. M.P., 126°–127° C.

NMR (CDCl$_3$, D$_6$-DMSO) δ (ppm): 7.42 (1H, d, J=10 Hz), 7.65 (1H, d, J=6 Hz).

IR $\nu_{max}^{nujol}$ (cm$^{-1}$): 3450.

In the practical usage of the hydantoins (I), they may be applied as such or in any preparation form such as wettable powders, emulsifiable concentrates, granules, suspensions or dusts.

For formulation of those preparations, a solid or liquid carrier or diluent may be used. As for the solid carrier or diluent, utilizable materials include mineral powders (e.g. kaolin, bentonite, montmorillonite, talc, diatomaceous earth, mica, vermiculite, gypsum, calcium carbonate, apatite, synthetic water-containing silicon hydroxide), vegetable powders (e.g. soybean powder, wheat flour, wooden powder, tobacco powder, starch, crystalline cellulose), high molecular weight compounds (e.g. petroleum resin, polyvinyl chloride, dammar gum, ketone resin), alumina, wax and the like.

As for the liquid carrier or diluent, there may be exemplified alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethyleneoxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts and the like. If necessary, gelatin, casein, sodium alginate, starch, agar, polyvinyl alcohol, ligninsulfonates or the like may be used as an auxiliary agent.

The hydantoins (I) of the invention may be used together with other herbicides to improve their activity as herbicides, and in some cases, a synergistic effect can be expected. Further, they may be also applied in combination with insecticides, nematocides, fungicides, plant growth regulators, fertilizers, etc. depending upon needs.

In the preparation of a herbicidal composition, the content of the hydantoins (I) may be from 1 to 95% by weight, preferably from 3 to 80% by weight.

Practical embodiments of the herbicidal composition according to the invention are illustratively shown in the following examples wherein parts and % are by weight. The compound number of the active ingredient corresponds to the one in Table 1.

PREPARATION EXAMPLE 1

Eighty parts of Compound No. 3, 3 parts of alkylsulfate, 2 parts of ligninsulfonate and 15 parts of hydrous silica are well mixed while being powdered to obtain a wettable powder.

PREPARATION EXAMPLE 2

Ten parts of Compound No. 5, 3 parts of alkylarylsulfate, 7 parts of polyoxyethylene alkylaryl ether, 60 parts of cyclohexanone and 20 parts of xylene are well mixed while being powdered to obtain an emulsifiable concentrate.

PREPARATION EXAMPLE 3

Five parts of Compound No. 6, 1 part of hydrous silica, 35 parts of bentonite and 59 parts of kaolin are well mixed while being powdered. The mixture is then kneaded with water, granulated and dried to obtain granules.

PREPARATION EXAMPLE 4

Three part of Compound No. 2, 0.3 part of isopropyl phosphate, 66.7 parts of kaolin and 30 parts of talc are well mixed while being powdered to obtain a dust.

PREPARATION EXAMPLE 5

Twenty parts of Compound No. 9 is mixed with 60 parts of of an aqueous solution containing 3% polyoxyethylene sorbitan monolaurate and grained until the particle size of the active ingredient becomes less than 3 microns. Twenty parts of an aqueous solution containing 3% of sodium alginate as a dispersing agent is incorporated therein to obtain a suspension.

The dosage rate of the hydantoins (I) may vary depending upon the particular compound, the sorts of cultivated plants, the modes of application, etc. Generally, however, the dosage rate is from 0.1 to 50 grams, preferably from 0.5 to 30 grams, of the active ingredient per are. The concentration of the active ingredient on the use may be usually from 0.01 to 5%, although this range is changeable depending on various factors as noted above.

The application of the hydantoins (I) as herbicides will be illustratively shown in the following Examples wherein the phytotoxicity to crop plants and the herbicidal activity on weeds were evaluated as follows: the aerial parts of the test plants were cut off and weighed (fresh weight); the percentage of the fresh weight of the treated plant to that of the untreated plant was calculated with the latter fresh weight taken as 100; and the phytotoxicity and the herbicidal activity were evaluated by the standard given in the table below. The rating values of phytotoxicity, 0 and 1, and those of herbicidal effect, 5 and 4, are generally regarded as satisfactory to protect crop plants and to control weeds, respectively. The rating values in the paddy field test alone were calculated from the dry weight of the test plants.

| Rating value | Fresh weight (percentage to untreated plot) (%) | |
|---|---|---|
| | Crop plant | Weeds |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

The following compounds were used in the Examples for comparison:

| Compound No. | Structure | Physical property | Remarks |
|---|---|---|---|
| a | [4-Cl-C6H4 substituted hydantoin with N—CH2CH=CH2] | M.P. 56.5°–57.5° C. | Japanese Patent Publn. No. 30695/1975 |
| b | [2,4-diCl-C6H3 substituted hydantoin with N—CH2CH=CH2] | $n_D^{25.0}$ 1.5868 | Japanese Patent Publn. No. 30695/1975 |
| c | [4-Cl-C6H4 substituted hydantoin with N—CH3] | M.P. 117.5°–118.5° C. | U.S. Pat. No. 3,134,663 |
| d | [4-Cl-2-(iso)C3H7O-C6H3 substituted hydantoin with N—C3H7(iso)] | $n_D^{20.5}$ 1.5261 | Compound synthesized for comparison |
| e | [2-Cl-4-Cl-5-(iso)C3H7O-C6H2 substituted hydantoin with N—C≡CH] | M.P. 99.0°–100.5° C. | Compound synthesized for comparison |

-continued

| Compound No. | Structure | Physical property | Remarks |
|---|---|---|---|
| f | 2,4-dichloro-5-(sec)C$_4$H$_9$O-phenyl-N linked to ring with N—C$_3$H$_7$(iso), two C=O groups | $n_D^{21.0}$ 1.5342 | Compound synthesized for comparison |
| g | 2,4-dichloro-5-(sec)C$_4$H$_9$O-phenyl-N linked to ring with N—C$_4$H$_9$(sec), two C=O groups | $n_D^{21.0}$ 1.5250 | Compound synthesized for comparison |
| h | 2,6-diethylphenyl-N(CH$_2$OCH$_3$)(COCH$_2$Cl) | | Commercially available herbicide known as "Alachlore" |
| i | (HO)$_2$P(O)—CH$_2$NHCH$_2$CO$_2$H | | Commercially available herbicide known as "Glyphosate" |

TEST EXAMPLE 1

Plastic beakers (diameter, 10 cm; height, 10 cm) were filled with upland field soil, and the seeds of barnyardgrass, wild oat, tall morningglory and velvetleaf were separately sowed in the beakers. A designed amount of the test compound formulated into an emulsifiable concentrate according to Preparation Example 2 and dispersed in water was sprayed over the top by means of a small hand sprayer at a spray volume of 5 liters per are. After the spraying, the test plants were grown for 20 days in the greenhouse, and herbicidal activity was examined. The results are shown in Table 5.

TABLE 5

| Compound No. | Dosage (weight of active ingredient, g/are) | Barnyardgrass | Wild oat | Tall morningglory | Velvetleaf |
|---|---|---|---|---|---|
| 1 | 20 | 5 | 5 | 5 | 5 |
|  | 10 | 5 | 5 | 5 | 5 |
| 2 | 20 | 5 | 5 | 4 | 5 |
|  | 10 | 5 | 5 | 4 | 5 |
| 3 | 20 | 5 | 5 | 5 | 5 |
|  | 10 | 5 | 5 | 4 | 5 |
| 4 | 20 | 5 | 5 | 5 | 5 |
|  | 10 | 5 | 5 | 5 | 5 |
| 5 | 20 | 5 | 5 | 5 | 5 |
|  | 10 | 5 | 5 | 5 | 5 |
| 6 | 20 | 5 | 5 | 5 | 5 |
|  | 10 | 5 | 5 | 4 | 5 |
| 7 | 20 | 5 | 5 | 5 | 5 |
|  | 10 | 5 | 5 | 5 | 5 |
| 8 | 20 | 5 | 5 | 5 | 5 |
|  | 10 | 5 | 5 | 4 | 5 |
| 9 | 20 | 5 | 5 | 5 | 5 |
|  | 10 | 5 | 5 | 5 | 5 |
| 10 | 20 | 5 | 5 | 5 | 5 |
|  | 10 | 5 | 5 | 5 | 5 |
| 11 | 20 | 5 | 5 | 4 | 5 |
| 12 | 20 | 5 | 5 | 4 | 5 |
|  | 10 | 5 | 4 | 4 | 5 |
| 13 | 20 | 5 | 5 | 5 | 5 |
|  | 10 | 5 | 5 | 5 | 5 |
| 14 | 20 | 5 | 5 | 4 | 5 |
|  | 10 | 4 | 4 | 4 | 5 |
| 15 | 20 | 5 | 5 | 5 | 5 |
|  | 10 | 5 | 5 | 4 | 5 |
| 16 | 20 | 5 | 5 | 5 | 5 |
|  | 10 | 5 | 5 | 4 | 5 |
| 17 | 20 | 5 | 5 | 5 | 5 |
|  | 10 | 5 | 5 | 5 | 5 |
| a | 40 | 4 | 2 | 1 | 4 |
|  | 20 | 3 | 1 | 0 | 4 |
| b | 40 | 4 | 3 | 1 | 5 |
|  | 20 | 2 | 1 | 0 | 4 |
| d | 40 | 3 | 2 | 3 | 4 |
|  | 20 | 1 | 0 | 1 | 3 |
| e | 40 | 0 | 0 | 0 | 1 |
|  | 20 | 0 | 0 | 0 | 0 |
| f | 40 | 3 | 2 | 1 | 4 |
|  | 20 | 1 | 0 | 0 | 2 |
| g | 40 | 2 | 0 | 0 | 3 |
|  | 20 | 1 | 0 | 0 | 1 |

TEST EXAMPLE 2

Plastic pots (500 ml volume) were filled with paddy field soil containing the seeds of barnyardgrass and hardstem bulrush and the seeds of broad-leaved weeds (e.g. monochoria, false pimpernel, toothcup), and water was poured therein until the depth of water became 4 cm. Rice seedlings of the 2-leaf stage and the buds of slender spikerush tided over the winter were transplanted therein and grown for 5 days in a greenhouse. A designed amount of the test compound formulated into an emulsifiable concentrate according to Preparation Example 2 was applied to the pots by perfusion. Thereafter, the test plants were grown for further 3 weeks in the greenhouse, and herbicidal activity and phytotoxicity were examined. The results are shown in Table 6. In this treatment, the emulsifiable concentrate was dispersed in water for application at a perfusion volume of 10 liters per are.

TABLE 6

| Compound No. | Dosage (weight of active ingredient, g/are) | Herbicidal activity | | | | Phytotoxicity |
| | | Barnyard-grass | Broad leaved weed | Slender spikerush | Hardstem bulrush | Rice Plant |
| --- | --- | --- | --- | --- | --- | --- |
| 4 | 2.5 | 5 | 5 | 4 | 5 | 1 |
| 5 | 2.5 | 5 | 5 | 5 | 5 | 1 |
| 6 | 2.5 | 5 | 5 | 4 | 5 | 1 |
| a | 5 | 0 | 3 | 1 | 1 | 0 |
| b | 5 | 1 | 3 | 2 | 1 | 0 |
| d | 5 | 0 | 4 | 1 | 3 | 0 |
| e | 5 | 0 | 4 | 0 | 1 | 0 |
| f | 5 | 3 | 4 | 2 | 1 | 0 |
| g | 5 | 0 | 4 | 2 | 2 | 0 |

TEST EXAMPLE 3

Plastic beakers (diameter, 10 cm; height, 10 cm) were filled with upland field soil, and the seeds of barnyardgrass, wild oat, wild mustard and velvetleaf were separately sowed in the beakers and grown for 2 weeks in a greenhouse. A designed amount of the test compound was sprayed to the foliage of the test plants by means of a small hand sprayer. After the spraying, the test plants were further grown for 3 weeks in the greenhouse, and herbicidal activity was examined. The results are shown in Table 7. In this treatment, the test compound was formulated into an emulsifiable concentrate according to Preparation Example 2 and applied at a spray volume of 5 liters per are by dispersing it in water with the addition of a spreading agent.

TABLE 7

| Compound No. | Dosage (weight of active ingredient, g/are) | Herbicidal activity | | | |
| | | Barnyard-grass | Wild oat | Wild mustard | Velvet-leaf |
| --- | --- | --- | --- | --- | --- |
| 4 | 5 | 5 | 5 | 5 | 5 |
|  | 2.5 | 5 | 5 | 5 | 5 |
| 6 | 5 | 5 | 5 | 5 | 5 |
|  | 2.5 | 5 | 5 | 5 | 5 |
| 7 | 5 | 5 | 5 | 5 | 5 |
|  | 2.5 | 5 | 5 | 5 | 5 |
| a | 5 | 1 | 0 | 0 | 4 |
|  | 2.5 | 0 | 0 | 0 | 2 |
| b | 5 | 0 | 0 | 0 | 4 |
|  | 2.5 | 0 | 0 | 0 | 1 |
| d | 5 | 0 | 0 | 0 | 4 |
|  | 2.5 | 0 | 0 | 0 | 1 |
| e | 5 | 0 | 0 | 0 | 1 |
|  | 2.5 | 0 | 0 | 0 | 0 |
| f | 5 | 0 | 0 | 0 | 5 |
|  | 2.5 | 0 | 0 | 0 | 4 |
| g | 5 | 1 | 0 | 0 | 3 |
|  | 2.5 | 0 | 0 | 0 | 1 |

TEST EXAMPLE 4

Plastic trays (35 cm×25 cm×15 cm) were filled with upland field soil, and the seeds of tall morningglory, velvetleaf, prickly sida, jimsonweed, black nightshade, redroot pigweed, Johnsongrass and green foxtail, and the seeds of cotton and soybean were sowed therein. A designed amount of the test compound formulated into a wettable powder according to Preparation Example 1 and dispersed in water was sprayed over the top by means of a small hand sprayer at a spray volume of 5 liters per are. After the spraying, the test plants were grown in a greenhouse for 20 days, and phytotoxicity and herbicidal activity were examined. The results are shown in Table 8.

TABLE 8

| Compound No. | Dosage (weight of active ingredient, g/are) | Herbicidal activity | | | | | | | | Phytotoxicity | |
| | | Tall morning-glory | Velvet-leaf | Prickly sida | Jimson-weed | Black night-shade | Redroot pigweed | Johnson-grass | Green foxtail | Cotton | Soybean |
| --- | --- | --- | --- | --- | --- | --- | --- | --- | --- | --- | --- |
| 1 | 5 | 3 | 5 | 5 | 5 | 5 | 5 | 5 | 5 | 1 | 1 |
| 4 | 10 | 4 | 5 | 5 | 5 | 5 | 5 | 5 | 5 | 1 | 0 |
|  | 5 | 4 | 5 | 5 | 5 | 5 | 5 | 4 | 5 | 0 | 0 |
| 5 | 10 | 5 | 5 | 5 | 5 | 5 | 5 | 5 | 5 | 1 | 1 |
|  | 5 | 4 | 5 | 5 | 5 | 5 | 5 | 5 | 5 | 1 | 1 |
| 7 | 5 | 3 | 5 | 5 | 5 | 5 | 5 | 5 | 5 | 0 | 1 |
| 9 | 5 | 3 | 4 | 5 | 5 | 5 | 5 | 5 | 5 | 1 | 0 |
| g | 20 | 1 | 0 | 2 | 0 | 4 | 5 | 2 | 5 | 0 | 0 |

TEST EXAMPLE 5

In a plastic pot (10 cm in diameter), upland soil was filled, and tubers of purple nutsedge (*Cyperus rotundus*) were transplanted at the depth of 2 cm from the soil surface and cultivated in a greenhouse for 4 weeks, whereby purple nutsedge was in 7-leaved stage. A designed amount of the test compound formulated into an emulsifiable concentrate according to Preparation Example 2 and diluted with water was applied to the foliage of the test plant by means of a hand sprayer, and the test plants were further grown in the greenhouse for 8 weeks and subjected to observation by removal of the soil with water. The herbicidal activity on the aerial part (e.g. leaves) and the underground part (e.g. rhizome and tuber) was evaluated according to the same criteria as in Test Example 1. The results are shown in Table 10.

TABLE 9

| Compound No. | Dosage of active ingredient g/are) | Herbicidal activity | |
|---|---|---|---|
| | | Aerial part | Underground part |
| 4 | 40 | 5 | 5 |
| | 20 | 5 | 4 |
| 5 | 40 | 5 | 4 |
| | 20 | 5 | 4 |
| 6 | 40 | 5 | 5 |
| | 20 | 4 | 4 |
| h | 40 | 5 | 4 |
| | 20 | 4 | 4 |

TEST EXAMPLE 6

Plastic beakers (diameter, 10 cm; height, 10 cm) were filled with upland field soil, and the seeds of barnyardgrass, large crabgrass, wild mustard and redroot pigweed were separately sowed in the beakers. A designed amount of the test compound was sprayed over the top by means of a small hand sprayer at a spray volume of 5 liters per are. After the spraying, the test plants were grown for 20 days in the greenhouse, and herbicidal activity was examined. The results are shown in Table 11. In this treatment, the test compounds were formulated into a wettable powder according to Preparation Example 1.

TABLE 10

| Compound No. | Dosage (weight of active ingredient, g/are) | Herbicidal activity | | | |
|---|---|---|---|---|---|
| | | Barnyardgrass | Large crabgrass | Wild mustard | Redroot pigweed |
| 4 | 20 | 5 | 5 | 5 | 5 |
| | 10 | 5 | 5 | 5 | 5 |
| o | 20 | 1 | 3 | 2 | 4 |
| | 10 | 0 | 1 | 1 | 3 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A phenyl isocyanate of the formula:

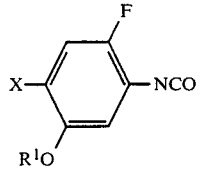

wherein X is a chlorine atom or a bromine atom and $R^1$ is a $C_1$–$C_4$ alkyl group, a cyclopropyl group, a $C_3$–$C_4$ alkenyl group or a $C_3$–$C_4$ alkynyl group.

2. A phenyl isocyanate as in claim 1, wherein $R^1$ is a methyl group, an ethyl group, an n-propyl group, an iso-propyl group, a sec-butyl group, an allyl group or a propargyl group.

3. A phenyl isocyanate as in claim 1, wherein X is chlorine and $R^1$ is isopropyl.

4. A phenyl isocyanate as in claim 1, wherein X is chlorine and $R^1$ is n-propyl.

5. A phenyl isocyanate as in claim 1, wherein X is chlorine and $R^1$ is methyl.

6. A phenyl isocyanate as in claim 1, wherein X is chlorine and $R^1$ is ethyl.

7. A phenyl isocyanate as in claim 1, wherein X is chlorine and $R^1$ is propene.

8. A phenyl isocyanate as in claim 1, wherein X is chlorine and $R^1$ is propyne.

9. A phenyl isocyanate as in claim 1, wherein X is chlorine and $R^1$ is sec-butyl.

* * * * *